United States Patent [19]

Nittner et al.

[11] Patent Number: 4,675,312

[45] Date of Patent: Jun. 23, 1987

[54] POLYSACCHARIDE AGGLOMERATE AND METHOD OF PREPARATION

[75] Inventors: Erich Nittner, Kreuzlinger; Jurg W. Hefel, Walzenhausen, both of Switzerland

[73] Assignee: Wheli Inter AG, Zug, Switzerland

[21] Appl. No.: 592,489

[22] Filed: Mar. 23, 1984

[30] Foreign Application Priority Data

Mar. 25, 1983 [CH] Switzerland ..................... 01647/83

[51] Int. Cl.⁴ ........................................... A61K 31/715
[52] U.S. Cl. ..................................... 514/54; 536/114
[58] Field of Search .................... 426/658; 514/54; 536/114

[56] References Cited

U.S. PATENT DOCUMENTS

| | | | |
|---|---|---|---|
| 3,455,899 | 7/1969 | Keen | 536/114 |
| 3,953,615 | 4/1976 | Gupta et al. | 426/658 |
| 3,978,245 | 8/1976 | Deininger et al. | 426/658 |
| 3,998,974 | 12/1976 | Zaffaroni | 536/114 |
| 4,031,305 | 6/1977 | DeMartino | 426/658 |
| 4,053,638 | 10/1977 | Litchfield et al. | 426/658 |
| 4,112,220 | 9/1978 | Carroll et al. | 536/114 |
| 4,156,021 | 5/1979 | Richardson | 426/658 |
| 4,315,918 | 2/1982 | Gayst et al. | 536/114 |
| 4,496,606 | 1/1985 | Michnowski | 426/658 |

FOREIGN PATENT DOCUMENTS 581296 8/1959 Canada ............................ 536/114

*Primary Examiner*—Johnnie R. Brown
*Attorney, Agent, or Firm*—Blum Kaplan

[57] ABSTRACT

A polysaccharide agglomerate formed from flour including galactomannans, such as guar and/or carob bean flour and an agglomeration agent, such as animal and/or vegetable products with high water-retention capacity is provided. The polysaccharide agglomerate is readily administered in dry form and rinsed down with liquid. This liquid taken to rinse down the agglomerate and intestinal secretions, independent of pH, cause the agglomerate to swell reaching full viscose volume after three to four hours.

12 Claims, No Drawings

POLYSACCHARIDE AGGLOMERATE AND METHOD OF PREPARATION

BACKGROUND OF THE INVENTION

This invention related to a polysaccharide agglomerate, and more particularly to a polysaccharide agglomerate based on flours including galactomannans and methods to prepare the agglomerate.

The medical significance of non-absorbable vegetable and soluble roughage as a food filler or additive has been known for a long time. The polysaccharides in particular, which fall under the heading glactomannans, possess valuable therapeutic properties. The therapeutic effects have been confirmed repeatedly in the literature. For example the following is a bibliography of recent sources: D. J. A. Jenkins, et al., Unabsorbable Carbohydrates and Diabetes: Decreased Post-Prandial Hyperglycaemia, Lancet (1976), 172–174; D. J. A. Jenkins, et al., Treatment of Diabetes with Guar Gum: Reduction of Urinary Glucose Loss in Diabetics, Lancet (1977) 779–780; T. M. S. Wolerer, et al., Guar Gum and Reduction of Post-Prandial Glycaemia: Effect of Incorporation into Solid Food, Liquid Food, and both, Br. J. Nutr. (1979), 41, 505–510; D. J. A. Jenkins et al., Dietary Fiber and Blood Lipids: Reduction of Serum Cholesterol in Type II Hyperlipidemia by Guar Gum, Am. J. Clin. Nutr. (11979), 32, 16–18; U. Smith and G. Holm, Effect of a Modified Guar Gum Preparation on Glucose and Lipid Levels in Diabetics and Healthy Volunteers, Atherosclerosis (1981); Guar Symposium, Pflanzenfasern-neue Wege in der Stoffwechseltherapie (Vegetable Fibers—New Directions in Metabolism Therapy), Munich, Feb. 3–5, 1983, Abstracts; (D. J. A. Jenkins and R. H. Taylor, The Therapeutic Use of Viscous Fiber; C. Leitzmann, Die Bedeutung der Pflanzenfasserstoffe in der modernen Ernahrung (The Significance of Vegetable Fibers in Present-Day Food); G. Neugebauer, et al., Interaktion von Guar mit Glibenclamid und Bezafibrat bei Besunden (The Interaction of Guar with Glibenclamid and Bezafibrat in Healthy Volunteers); B. Lembcke et al., Digoxin-Bioverfugbarkeit unter dem Einfluss von Guar (Digoxin Bio-Availability under the Influence of Guar); H. Kasper et al., Der Effekt Van Guar auf die Gerinnung beigleichzeitiger Gabe von Phenprocoumon (The Effect of Guar on Coagulation with Simultaneous Administration of Phenprocoumon); W. E. Hansen et al., Der Einfluss von Guar auf die Gallenblasenkontraktion und Serumgallensauren-Konzentration (The Effect of Guar on Gall Bladder Contraction and Serum Gall Acid Concentration); A. E. Harmuth-Hoene, Der Einfluss von Guar auf die Stickstoffbilanz, die Resorption von Mineralstoffen und Spurenelementen, unde die verdauliche Energie beim Menschen (The Effect of Guar on the Nitrogen Balance, the Resorption of Minerals and Trace Elements, and the Digestive Energie in Humans); C. Najemnik et al., Klinische Untersuchung zum Effekt von Guar auf Lipide, Lipoproteine und Korpergewicht bei Patienten mit primarer Hyperlipidaemie Type II. (Clinical Investigation of the Effect of Guar on Lipids, Lipoprotein and Body Weight in Patients with Primary Type II Hyperlipidemia); A Wirth et al., Einfluss einer kombinierten Verabreichung von Guar-Bezafibrat auf Lipide, Apolipoproteine und Lipoproteine bei Patienten mit primarer Hyperlipoproteinamie Type II (The Effect of Combined Concentration of Guar-Bezafibrat on Lipids, Apolipoprotein and Lipoprotein in Patients with Primary Type II Hyperlipiproteinemia); J. Schrezenmeier at al., Die Bedeutung van Guar fur die Behandlung gastroenterologischer Erkrankungen (The Significance of Guar in the Treatment of Gastroenterological Disorders); M. U. Schneider et al., Einfluss von Guar auf die lipolytische und proteolytische Exokrine Pankreasfunktion in Vitro und in Vivo (The Effect of Guar on the Lipolytic and Proteolytic Exocrine Pancreas Function in Vitro and in Vivo); W. E. Hansen and G. Schultz, Losliche unde fixierte Inhibitoren der Amylase in Guar und anderen Ballaststoffen (Soluble and Fixed Inhibitors of Amylase in Guar and Other Roughage); K. Huth, Guar-Therapie bei Diabetes mellitus (Guar Therapy for Diabetes Mellitus); H. Laube et al., Multizenterstudie zum Effekt von Guar auf Kohlenhydrat-, Lipidstoffwechsel und Vertraglichkeit bei Ambulanten Patienten mit manifestem Diabetes mellitus (Multi-Center Study on the Effect of Guar on Carbohydrate and Lipid Metabolism and Tolerance in Outpatients with Overt Diabetes Mellitus); S. Ehrhardt-Schmelzer et al., Kontrollierte Studie uber den Effekt Von Guar bei Diabetikern (Controlled Study on the Effect of Guar on Diabetics); H. D. Klimm et al., 1-Jahres-Untersuchung zum Effekt von Guar auf Kohlenhydrat-, Lipidstoffwechsel und Vertraglishkeit bei ambulanten, Sulfonylharnstoff-behandelten Diabetikern (One-year Study on the Effect of Guar on Carbohydrate and Lipid Metabolism and Tolerance in Outpatients under Sulfonyl Urea Treatment for Diabetes); D. B. Jones et al., Clinical Evaluation of the Effect of 5 gms BMO 3003 (Guar) B.I.D. on Carbohydrate and Lipid Metabolism in Outpatients with Overt Diabetes Melliltus); A. Aro et al., Departments of Medicine and Clinical Chemistry, University of Kuopio, SF-70210 Kuopio 21, Finland, Improved Diabetic Control and Hypocholesterolaemic Effect induced by long-term Dietary Supplementation with Guar Gum in Type 2 (Insulin-Independent) Diabetes; W.-J. L. Chen and J. W. Anderson, Medical Service, University Kentucky, College of Medicine, Lexington, Ky. 40507, Effects on Guar Gum and Wheat Bran on Lipid Metobolism of Rats; D. J. A. Jenkins et al., Combined Use of Guar and Acarbose in Reduction of Postprandial Glycaemia, Lancet (1979), 924–927; D. J. A. Jenkins, Dietary Fibre, Diabetes, and Hyperlipidaemia, Lancet, (1979), 1287–1289; D. J. A. Jenkins et al., Improved Glucose Tolerance four hours after taking Guar with Glucose, Diabetologia 19, 21–24 (11980); L. M. Morgan et al., The Effect of Unabsorbable Carbohydrate on Gut Hormones, Diabetologia 17, 85–89 (1979).

At present, dietary preparations including galactomannans are commercially available in the form of pastes or slurrys. These are generally administered orally. However, oral administration of these preparations in dry form is not possible without problems due to the stickiness and viscosity of the preparations. Thus, none of the available products provide all the properties in a desirable way, namely trouble-free administration and maintaining optimum effectiveness.

Accordingly, it is desirable to provide a preparation which will contain an effective mixture yet be easy to administer. Additionally, with the aid of the liquid used to rinse down the agglomerate and the intestinal secretions in the stomach and the intestinal tract, the agglomerate should swell rapidly into a large-viscous volume.

SUMMARY OF THE INVENTION

Generally speaking, a polysaccharide agglomerate prepared in accordance with the invention includes from about 60 to 95 parts of a glactomannan-containing flours and from about 5 to 40 parts of an agglomeration agent is provided. The galactomannans are those flours including polysaccharides that yield galactose and mannose on hydrolysis, such as guar and/or carob bean flour. The agglomeration agents include animal and/or vegetable matter having a high water-retaining capacity. The agglomerate may include additional aromatic, taste and coloring agents.

The polysaccharide agglomerate prepared in accordance with the invention, due to a delayed swelling start, is easily administered in dry form. Liquid is generally taken to rinse down the agglomerate. This liquid and intestinal secretions, independent of the changing pH values in the intestinal tract, cause the polysaccharide agglomerate to swell and reach full viscous volume after three to four hours. The high swelling and water-retention capacity, as well as the viscous properties, cause considerable delay in the metabolism in the digestive tract. In view of this delay, the galactomannans cannot be metabolized by enzymes and are only to a small extend affected by bacteria in the intestines. The binding, swelling and sliding agents are particularly valuable in dietary treatments for treating a wide range of metabolist disorders. Generally in order to impart an actual effect on the metabolism, dosages from a minimum effective amount up to about 30 grams per day are utilized.

The polysaccharide agglomerate is prepared by placing an agglomeration agent in a mixer and adding a glactomannan containing flour while stirring until homogenous. The mixture is dried and sifted. Alternatively, dried agglomeration agents and vehicles may be placed in a mixer with water and galactomannan flour added until homogeneous. The mixture is then dried and sifted.

Accordingly, it is an object of the invention to provide an improved dietary product including glactomannans.

It is another object of the invention to provide an improved polysaccharide agglomerate.

It is a further object of the invention to provide an improved polysaccharide agglomerate containing a galactomannan containing flour and an agglomeration agent.

Still another object of the invention is to provide a method for preparing improved dietary products including galactomannans.

Still other objects and advantages of the invention will in part be obvious and will in part be apparent from the specification.

The invention accordingly comprises the several steps and the relation of one or more of such steps with respect to each of the others, and the composition possessing the features, properties and the relation of constituents which are exemplified in the following detailed disclosure and the scope of the invention will be indicated in the claims.

DESCRIPTION OF THE PREFERRED EMBODIMENTS

The polysaccharide agglomerate prepared in accordance with the invention includes at least one galactomannan containing material and at least one agglomeration agent. The polysaccharide agglomerate after being administered is characterized by a delayed swelling start. Thus, it can be readily administered in dry form. After a time, the liquid taken to rinse it down and the intestinal secretions, independent of the changing pH value of the intestinal tract, cause the polysaccharide agglomerate to swell continuously until it reaches it full volume after three to four hours. The polysaccharide agglomerate in accordance with the invention includes flours containing polysaccharides which yield galactose and mannose on hydrolysis. Preferably the flour containing galactomannans is guar flour, carob bean flour and mixtures thereof.

The agglomeration agent is an animal or vegetable substance having a high water-retaining capacity. Among the most suitable and preferred materials are, for example, milk, potatoe, fruit and citrus paste, in their wet or dry form.

Generally speaking, the polysaccharide agglomerate in accordance with the invention includes from about 60 to 95 parts flour containing galactomannans and from about 5 to 40 parts agglomeration agent. These parts are by weight, based on the dry weight of the polysaccharide agglomerate formed.

Additional aromatic, taste and coloring agents may be added in the usual manner.

The polysaccharide agglomerate in accordance with the invention may be prepared as follows.

1. The agglomeration agent in the form of a fine, watery paste is placed in a batter mixer. The flour containing galactomannan is added under stirring. The mixture is agitated until it becomes homogeneous. At that time the mixture is dried and sifted.

2. Dry agglomeration agent is placed in a batter mixer with sufficient water to thicken. After thickening, flour containing galactomananns is added under mixing and the mixed is mixture until homogeneous. At that time, the mixture is dried and separated by sifting.

The following examples are set forth to illustrate the polysaccharide agglomerate and method of preparation in accordance with the invention. These examples are not set forth in a limiting sense.

EXAMPLE 1

An agglomeration agent was prepared in a blender by adding 60 kg peeled potatoes and 18 kg peeled apples and mixing. While continuing mixing, 25.8 kg of guar flour containing galactomannans was added at room temperature. As soon as the texture of the mixture was homogeneous and free of lumps, the mixture was carefully dried in an air circulating oven at 80° C. After drying the dry product was sifted to yield the polysaccharide agglomerate in accordance with the invention.

EXAMPLE 2

Into a batter mixer was added 10.8 kg dried potatoes and 14.4 kg dried apples. To this mixture was added 50 kg of water and the mixture was mixed until there was a homogeneous batter. At this time, 25 kg of guar flour containing galactomannans was added and mixed until the mixture was uniform and free of lumps. The mixture was then dried with circulating air flow and sifted to yield the polysaccharide agglomerate in accordance with the invention.

Without further treatment, the polysaccharide agglomerates prepared in Example 1 and Example 2 were ready for use. They were readily administered orally in dry form in a dose of 7 grams rinsed down with 200 ml water or juice as the liquid.

Generally, from about 5 to 100 ml of liquid, and preferably from about 10 to 40 ml of liquid per gram of agglomerate is taken to rinse down the agglomerate.

EXAMPLE 3

When the polysaccharide agglomerates of the type prepared in Examples 1 and 2 were placed in artifical gastric fluids under gentle agitation at 37° to 39° C., after an initial delay swelling occurs continuously. This continuous swelling occurs in both an acid pH environment and, after one hour, also in an alkaline pH environment. After three to four hours, the polysaccharide agglomerate swelling reaches its full, viscous volume.

The particularly high swelling and water-retention capacity as well as the viscous properties of the polysaccharide agglomerate in accordance with the invention, causes a considerable delay in the metabolism in the digestive tract. Thus, the galactomannans present in the agglomerate cannot be catabolized by enzymes and fermenting agents in the body, but only to a small extent by bacteria present in the intestines. The binding, swelling and sliding effects are particularly valuable in dietary treatments and for treating a wide range of metabolism disorders. In order to obtain the beneficial effects on the metabolism, dosages from a minimum effective amount of about 7 grams per day up to about 30 g per day are suitable. Administration of larger daily doses is not recommended due to the strong swelling and viscous property of the product.

It will thus be seen that the objects set forth above, among those made apparent from the preceding description are efficiently attained and since certain changes may be made in carrying out the above process and in the composition set forth without departing from the spirit and scope of the inventin, it is intended that all matter contained in the above description shall be interpreted as illustrative and not in a limiting sense.

It is also to be understood that the following claims are intended to cover all of the generic and specific features of the inventin herein described and all statements of the scope of the invention which, as a matter of language, might be said to fall therebetween.

Particularly, it is to be understood that in said claims, ingredients or compounds recited in the singular are intended to include compatible mixtures of such ingredients wherever the sense permits.

What is claimed is:

1. A polysaccharide agglomerate for providing delay in metabolism in the digestive tract, consisting essentially of between about 60 and 95% by weight of a galactomannans containing material selected from the group consisting of guar fluor, carob bean flour, and mixtures thereof admixed with between about 5 and 40% by weight of at least one agglomeration agent selected from the group consisting of milk, potatoes, fruit and citrus paste, whereby after oral administration the agglomerate swells continuously in the intestinal tract, independent of pH, until it reaches its full viscous volume after about 3 to 4 hours.

2. The polysaccharide agglomerate of claim 1, wherein the polysaccharide agglomerate is a granulate.

3. A method of lowering the metabolism in the digestive tract, comprising administering orally a polysaccharide agglomerate including about 60 to 95% by weight of a galactomannans containing material selected from the group consisting of guar flour, carob bean flour and mixtures thereof admixed with about 5 to 40% by weight of an agglomeration agent selected from the group consisting of milk, potatoes, fruit and citrus fruit, whereby after oral administration the agglomerate swells continuously in the intestinal tract, independent of pH, until it reaches its full viscous volume after about 3 to 4 hours.

4. The method of claim 3, wherein the polysaccharide agglomerate is a granulate.

5. The method of claim 3, wherein between from about 7 grams to about 30 grams per day of the agglomerate are administered.

6. The method of claim 3, further including administering between about 5 to 100 ml of a liquid per gram of agglomerate to rinse down the agglomerate.

7. The method of claim 6, further including administering between from about 10 to 40 ml of liquid per gram of agglomerate administered.

8. A polysaccharide agglomerate for providing delay in metabolism in the digestive tract consisting essentially of:

between about 60 and 95% by weight of a galactomannans containing material selected from the group consisting of guar flour, carob bean flour and mixtures thereof;

a first agglomeration agent selected from the group consisting of milk, potatoes, fruit and citrus paste; and a second agglomeration agent that is different from the first agglomeration agent and is selected from the group consisting of milk, potatoes, fruit and citrus;

whereby the total percent by weight of the first and second agglomeration agents is between about 5 and 40% and the first and second agglomeration agents act in a synergistic manner to effect the formation of a granulate and delay of the swelling process.

9. The polysaccharide agglomerate of claim 8, wherein the first agglomeration agent is selected from the group consisting of fruit and citrus paste.

10. The polysaccharide agglomerate of claim 8, wherein the second agglomeration agent is selected from the group consisting of milk and potatoes.

11. The polysaccharide agglomerate of claim 8, wherein the first agglomeration agent is dried fruit and the second agglomeration agent is dried potatoes.

12. The polysaccharide agglomerate of claim 11, wherein the dried fruit is dried apples.

* * * * *